United States Patent
Will

(10) Patent No.: US 9,371,524 B2
(45) Date of Patent: Jun. 21, 2016

(54) AMINE COMPOUNDS FOR THE SELECTIVE PREPARATION OF BIOLOGICAL SAMPLES

(71) Applicant: Roche Molecular Systems, Inc., Pleasanton, CA (US)

(72) Inventor: Stephen Gordon Will, Cham (CH)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 231 days.

(21) Appl. No.: 13/856,922

(22) Filed: Apr. 4, 2013

(65) Prior Publication Data

US 2013/0266951 A1 Oct. 10, 2013

(30) Foreign Application Priority Data

Apr. 5, 2012 (EP) ..................... 12163497

(51) Int. Cl.
*C12Q 1/68* (2006.01)
*C12N 15/10* (2006.01)

(52) U.S. Cl.
CPC .......... *C12N 15/101* (2013.01); *C12N 15/1006* (2013.01); *C12N 15/1013* (2013.01)

(58) Field of Classification Search
CPC .......................... C12N 15/1006; C12N 15/101
USPC .............. 435/6.1, 7.1, 7.2; 422/430
See application file for complete search history.

(56) References Cited

U.S. PATENT DOCUMENTS

2010/0120171 A1* 5/2010 Vilgrain et al. ............... 436/501

FOREIGN PATENT DOCUMENTS

| CN | 200910307632.1 A | 3/2010 |
|---|---|---|
| EP | 1031626 B1 | 1/2011 |
| WO | 9418156 A1 | 8/1994 |
| WO | 9522389 A1 | 8/1995 |
| WO | 9819709 A2 | 5/1998 |
| WO | 9819709 A3 | 5/1998 |
| WO | 9823645 A1 | 6/1998 |
| WO | 0200600 A1 | 1/2002 |
| WO | 2004081175 A2 | 9/2004 |
| WO | 2004081175 A3 | 9/2004 |
| WO | 2004101809 A2 | 11/2004 |
| WO | 2004101809 A3 | 11/2004 |
| WO | 2006034294 A1 | 3/2006 |
| WO | 2006103094 A2 | 10/2006 |
| WO | 2006103094 A3 | 10/2006 |
| WO | 2012013733 A1 | 2/2012 |

OTHER PUBLICATIONS

Qiagen, Jun. 2005, "QIAprep(R) Miniprep Handbook: For purification of molecular biology grade DNA", 2nd Edition; www.qiagen.com.
"Elimination of plasmids pKM 101 and F'lac from *Salmonella typhimurium* and *Escherichia coli* by by bisammonium salt. The effect of outer membrane pattern", XP002111379, retrieved from STN Chemical Abstract, Database accession No. 115-275625, 1991.
"Interaction of DNA and DNA-calcium-model phosphatidylcholine membrane complex with surface active bisammonium salts", XP002111380, retrieved from STN Chemical Abstrac, Database accession No. 110-20127, 1988.

* cited by examiner

*Primary Examiner* — Jezia Riley
(74) *Attorney, Agent, or Firm* — Carol Johns; M. Reza Savari

(57) ABSTRACT

A method for isolating a biological target material from a biological sample is provided, the method including binding the target material to a solid support, wherein impurities are selectively removed from the solid support by washing the latter with a wash buffer containing a cationic amine. A kit for isolating a biological target material from a biological sample is also provided, the kit including a wash buffer containing a cationic amine, and the use of a respective wash buffer.

7 Claims, 5 Drawing Sheets

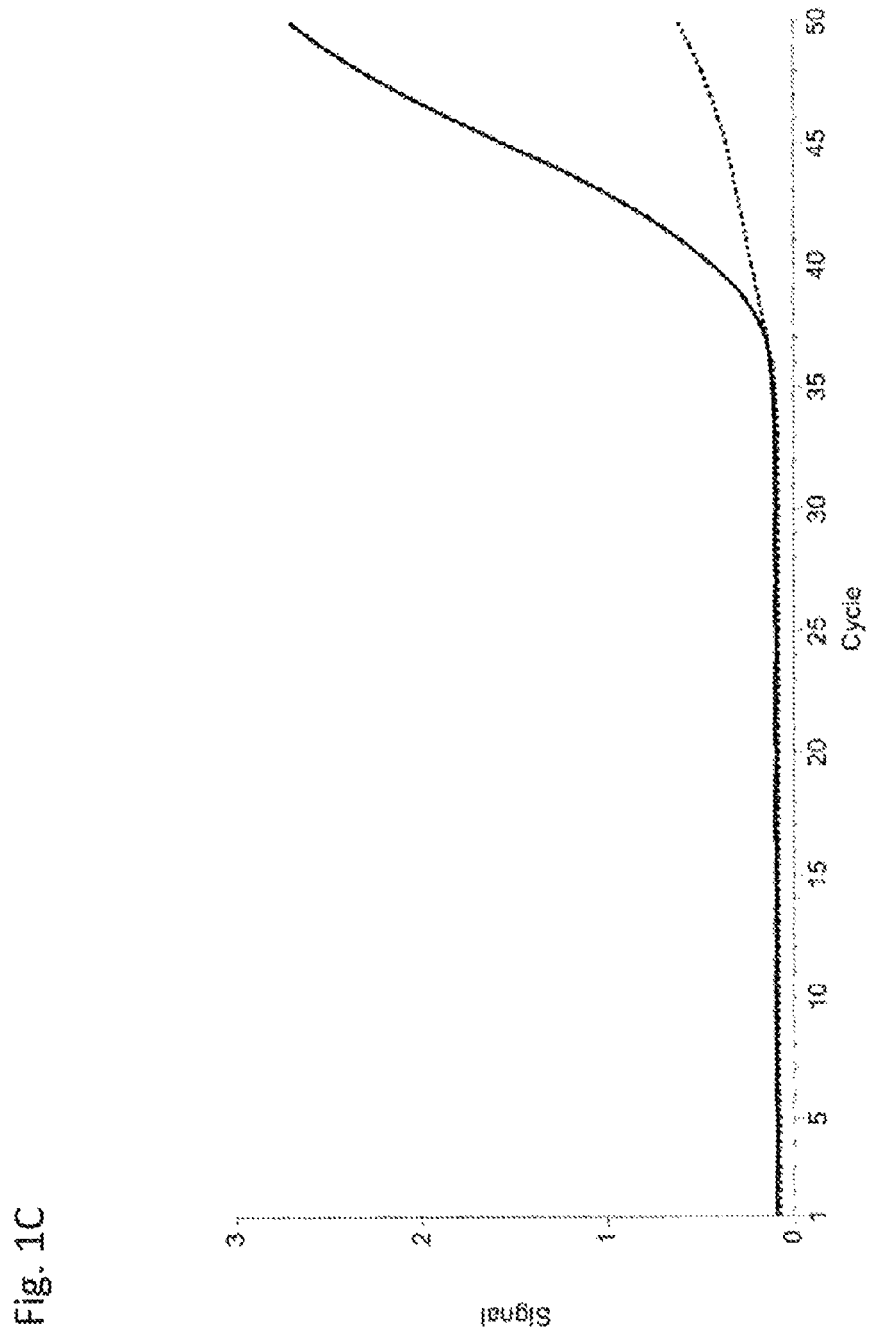

AMINE COMPOUNDS FOR THE SELECTIVE PREPARATION OF BIOLOGICAL SAMPLES

CROSS-REFERENCES TO RELATED APPLICATIONS

The present application claims the benefit of priority under 35 U.S.C. §119 of EP12163497.6, filed Apr. 5, 2012, the content of which is incorporated by reference herein in its entirety.

FIELD OF THE INVENTION

The present invention relates to the field of analytics. Within this field, it concerns the isolation of biological target material, from a biological sample comprising binding said target material to a solid support, wherein impurities are selectively removed from the solid support by washing the latter with a washing buffer containing a cationic amine.

BACKGROUND OF THE INVENTION

The isolation of biological materials such as nucleic acids or proteins from complex biological mixtures such as clinical samples, e.g., whole blood, is of considerable significance especially for diagnostic purposes.

Numerous different methods have been developed in the art, e.g., denaturing, precipitating and removing undesired components in a sample with subsequent precipitation and isolation of the analyte in question (for example alcohol-based precipitation of nucleic acids).

Another approach is the binding of the biological material to be isolated to a solid support material which may be provided, e.g., in the form of chromatographic columns.

For diagnostic purposes, and especially for the automated isolation of biological materials subject to subsequent medium- or high-throughput analysis, binding particles are often used.

It is known in the art that during the isolation process often impurities are bound to the respective solid support and thus become co-isolated, and such impurities may interfere with downstream analysis of the biological material in question.

The prior art has attempted to deal with the above-mentioned circumstance by applying various measures.

For instance, the QIAprep® Miniprep Handbook (2nd Edition, December 2006) discloses a process in which the solid support is washed with chaotropic salts and ethanol, and CN101665785A discloses a solid support wash buffer containing Triton X-100. These approaches exhibit various drawbacks.

SUMMARY OF THE INVENTION

In a first aspect, as set out supra, an embodiment of the invention relates to a method for isolating a biological target material from a fluid sample.

This method comprises, in a first step, combining together a solid support and the fluid sample in a reaction vessel such that the biological target material can bind to the solid support. Subsequently, the solid support material is isolated from the other material present in the fluid sample in a separation station, followed by purification of the biological target material by separating the fluid sample from the solid support material. Then, the solid support material is washed one or more times with a wash buffer comprising a cationic amine.

Furthermore, an embodiment of the invention provides the use of a wash buffer comprising a cationic amine for selectively removing an inhibitor of the analysis of a biological target material from a solid support to which said biological target material is bound.

Another embodiment of the present invention is a kit for isolating a biological target material from a fluid sample, said kit comprising the components:
 a binding buffer
 a solid support
 a washing buffer comprising a cationic amine
 optionally an elution buffer,
wherein the binding buffer and the washing buffer are different buffers contained in different vessels.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

FIGS. 1A-1D show different PCR growth curves of a Full Process Control (FPC) and an Inhibition Control (IC). The FPC was recovered from whole blood using a wish buffer containing putrescine dihydrochloride at a concentration of 22 mM or a reference wash buffer, respectively, the latter without a cationic amine but otherwise identically formulated. The IC was spiked directly into the PCR mastermix.

FIG. 1A shows PCR growth curves of a DNA Full Process Control (FPC) recovered using a wash buffer with putrescine (solid line) and a reference wash buffer without cationic amine (dotted line). The curves clearly show an improved result with the amine-containing wash-buffer, suggesting a significantly improved DNA recovery during sample preparation.

FIG. 1B shows PCR growth curves of a DNA Inhibition Control (IC) spiked into the PCR mastermix after using in the sample preparation a wash buffer with putrescine (solid line) and a reference wash buffer without cationic amine (dotted line). The result shows that PCR performance is comparable in both cases.

FIG. 1C shows PCR growth curves of an RNA Full Process Control (FPC) recovered using a wash buffer with putrescine (solid line) and a reference wash buffer without cationic amine (dotted line). The curves clearly show an improved result with the amine-containing wash-buffer, suggesting a significantly improved RNA recovery during sample preparation.

FIG. 1D shows PCR growth curves of an RNA Inhibition Control (IC) spiked into the PCR mastermix after using in the sample preparation a wash buffer with putrescine (solid line) and a reference wash buffer without cationic amine (dotted line). The result shows that PCR performance is comparable in both cases.

DETAILED DESCRIPTION OF THE INVENTION

Figure 1A:
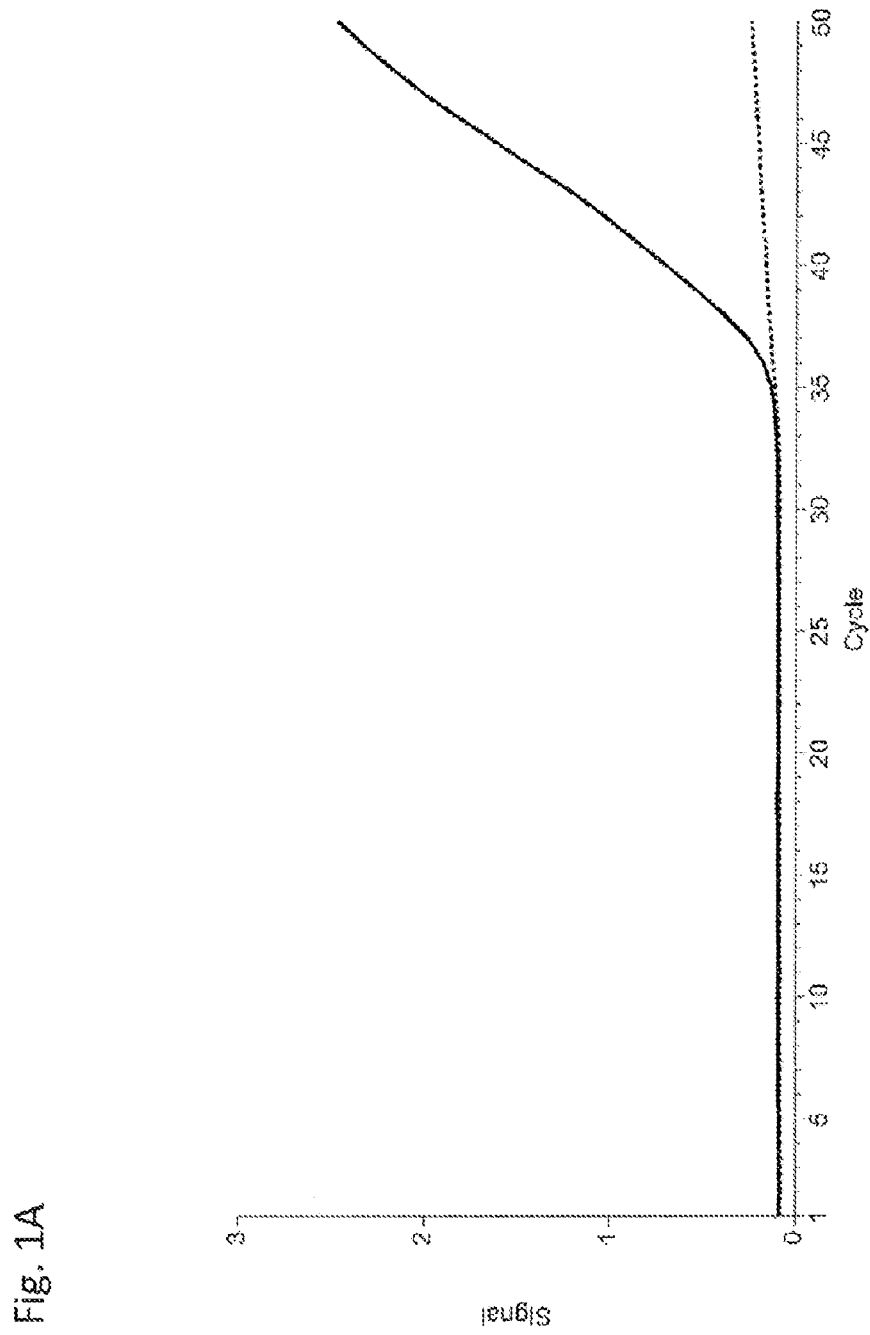

As mentioned above, the present invention relates in a first aspect to a method for isolating a biological target material from a fluid sample, said method comprising the steps:

a. combining together a solid support and said fluid sample in a reaction vessel for a period of time and under conditions sufficient to permit said biological target material to be immobilized on the solid support, b. isolating the solid support from the other material present in the fluid sample in a separation station, c. purifying the biological material by separating the fluid sample from the solid support, d. washing the solid support one or more times with a wash buffer comprising a cationic amine.

As outlined above, a frequent prerequisite for a successful diagnostic test is the isolation of substantially undegraded biological material without the co-isolation of significant amounts of impurities that may interfere with downstream processing of said target material. This can be the case e.g. during the isolation and analysis of proteins or nucleic acids.

The terms "nucleic acid" or "polynucleotide" can be used interchangeably and refer to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (Science 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

Some of the most widely used analysis methods for nucleic acids, such as e.g. PCR (see e.g. PCR Protocols: A Guide to Methods and Applications; eds. Innis et al., Academic Press, San Diego, USA, 1990), involve amplification of the target molecule.

The term "amplification" generally refers to the production of a plurality of nucleic acid molecules from a target nucleic acid wherein primers hybridize to specific sites on the target nucleic acid molecules in order to provide an initiation site for extension by a polymerase. Amplification can be carried out by any method generally known in the art, such as but not limited to: standard PCR, long PCR, hot start PCR, qPCR, RT-PCR and Isothermal Amplification.

The enzymes bringing about said amplification are prone to inhibition by various substances contained in complex biological samples such as e.g. whole blood. In consequence, if a nucleic acid amplification fails due to inhibition and thus e.g. a pathogen in a clinical sample is not detected, then this may invoke severe consequences for the patient in question. Such a "false negative result" may cause that a patient does not receive treatment for an undetected disease that might be life-threatening in certain cases.

In order to try to avoid the co-isolation of impurities that may inhibit downstream analysis of the biological target material, the prior art has adopted various approaches such as the ones mentioned supra, comprising washing the solid support to which the biological target material is bound with wash buffers containing e.g. chaotropic agents, ethanol or detergents like Triton X-100.

However, these substances themselves are all known inhibitors of PCR and are also detrimental to other analytic methods. Hence, having such substances in a wash buffer can either inhibit the downstream analytics by itself, or it can render further wash steps mandatory in order to remove these components again, thus making the respective isolation process more complicated and most likely more expensive. Also, every additional step delays the time until a result is obtained, which can be a critical factor especially in the field of in-vitro diagnosis.

Moreover, some impurities acting as inhibitors to analytic methods cannot be efficiently removed by the measures disclosed in the prior art as described above. In this context, especially whole blood constitutes a considerable challenge due to its complex composition.

A common strategy to address this problem has been to reduce the input quantity of the biological sample. This attempts to reduce the input level of the inhibitory impurity which would reduce its concentration in the output of the isolation process. This has the undesirable consequence of also reducing the concentration of the target analyte, which may adversely affect the limit of detection of the analysis method.

Alternatively, the impact of the inhibitors in the liquid product from the isolation process may be reduced by dilution of the eluate to such concentrations that the downstream analysis method is unaffected by the residual concentration of the inhibitor. This potential benefit may also be gained through the reduction in the volume of the eluate used in downstream analyses. Both of these methods reduce the concentration of the inhibitors in the downstream analyses, but with a concomitant reduction in concentration of the biological target material under study. This can negatively affect the sensitivity of the downstream analyses.

The skilled artisan will appreciate the value of a method for the selective removal of inhibitors during the isolation process, which will allow either the use of an increased volume of the input biological sample or obviate the need for dilution of the eluate from the isolation. Alternative methods for the relief of inhibition include the flocculation of proteinaceous materials from the biological material. Other methods include the use of glycosylases to degrade polysaccharides which may act as inhibitors of downstream analyses. Both of these methods are intended to address large molecules which may act as inhibitors. The skilled artisan will appreciate the value of a method for the removal of inhibitors of a broad range of molecular sizes.

The method according to the present invention efficiently reduces the co-isolation of impurities. By washing the solid support with a wash buffer comprising a cationic amine, impurities that may interfere with downstream processing such as analysis of the isolated target material are removed while retaining the biological target material bound to the solid phase.

Among the advantages of the method described above is its capability to efficiently remove certain inhibitors which are particularly detrimental to analysis methods such as nucleic acid amplification like PCR. Hemin, a breakdown product of hemoglobin comprising the oxygen-binding portion of the latter, is abundant in many whole blood samples, since it is often released from lysed erythrocytes e.g. during storage. Hemin has considerable affinity to solid supports to which e.g. nucleic acids bind. Therefore, co-isolation of hemin with nucleic acids is a problem when analyzing nucleic acids from a whole blood sample, especially since it is a strong inhibitor of analytical techniques like PCR.

As shown in Table 1, applying a wash buffer with a cationic amine according to the method described above enables the person skilled in the art to remove hemin from the solid support such that the reaction conditions for downstream analysis are improved.

Moreover, the method described above is suited to remove other inhibitory impurities such as e.g. bilirubin, humic acid, melanin or bile salts.

Figure 1B:
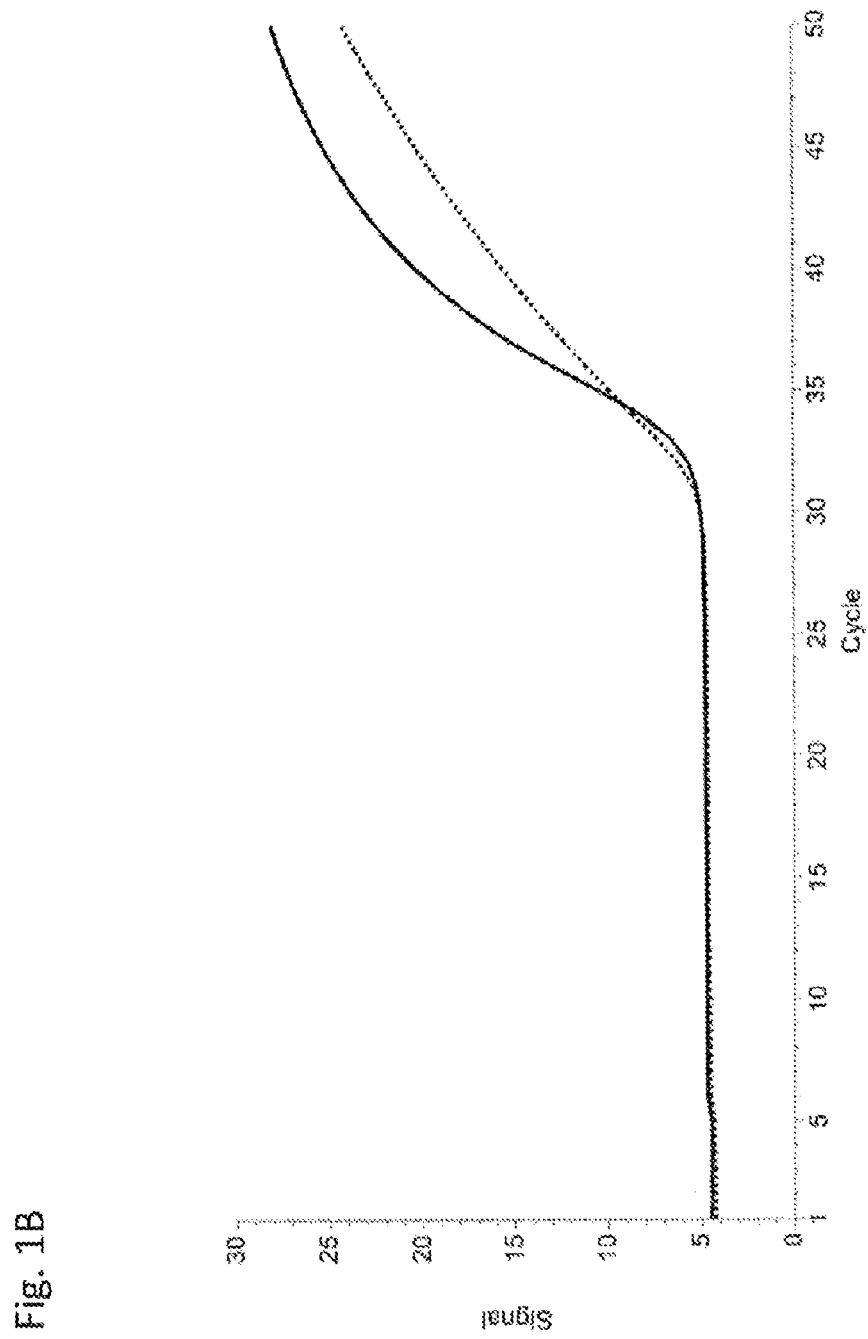
Figure 1D:
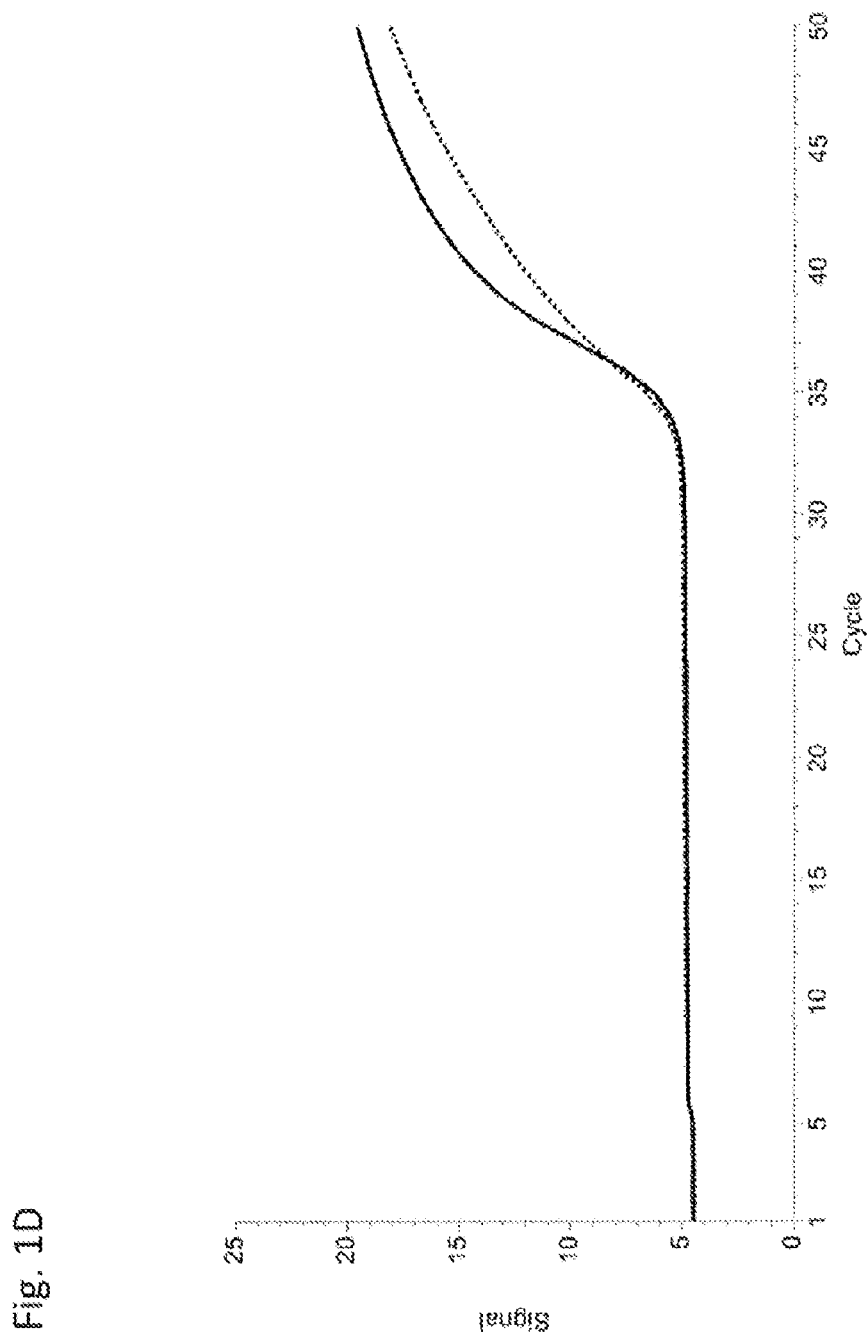

Also, the method described supra does not by itself interfere with downstream analytics. In FIG. 1, it is shown that a PCR carried out on a nucleic acid isolated from blood or plasma by the method described above is significantly improved as compared to a method using a wash buffer without a cationic amine.

In the context of the present invention, the terms "isolation", "purification" or "extraction" of a biological target material relate to the following: Before biological target materials like e.g. nucleic acids may be analyzed in a diagnostic assay e.g. by amplification, they typically have to be purified, isolated or extracted from biological samples containing complex mixtures of different components. Suitable methods are known to the person skilled in the art.

Typically, one of the first steps comprises releasing the contents of cells or viral particles e.g. by using enzymes and/or chemical reagents. This process is commonly referred to as lysis. For enrichment of the analyte in question in the lysate, one useful procedure for binding nucleic acids entails the selective binding of nucleic acids to glass surfaces of binding particles such as e.g. magnetic particles in chaotropic salt solutions and separating the nucleic acids from contaminants such as agarose, proteins or cell debris. In some embodiments, the glass of the particles is formed using the gel sol process described in WO 96/41811.

"Biological target material" or "biological material", in the sense of the invention, comprises all kinds of biological molecules, for example proteins or nucleic acids, but also other molecules occurring in nature or being derivatives or synthetic analogues or variants thereof. Furthermore, the term "biological material" comprises viruses and eukaryotic and prokaryotic cells.

A "fluid sample" is any fluid material that can be subjected to a diagnostic assay and is in some embodiments derived from a biological source. A fluid sample can be pipetted, such that the term "fluid sample" comprises homogeneous or homogenized liquids, but also emulsions, suspensions and the like. In some embodiments, said fluid sample is derived from a human and is a body liquid. In an embodiment of the invention, the fluid sample is human blood or blood plasma, urine, sputum, sweat, genital or buccal or nasal swabs, pipettable stool, or spinal fluid. In other embodiments, the fluid sample is human blood or blood plasma.

The term "solid support" comprises any materials suited for binding to the biological target material, e.g. magnetic particles with our without glass coating, silica gel, glass fibers, glass fiber filters, filter paper etc., while the solid support is not limited to these materials. The solid support can be provided in the form e.g. of chromatographic columns, binding membranes in vessels, binding particles such as e.g. beads, or the like.

In some embodiments of the method described above, the solid support comprises nucleic acid binding particles, in further embodiments one or more of the materials selected from silica, metal, metal oxides, plastic, polymers and capture oligonucleotides. In yet further embodiments the solid support is magnetic glass particles.

The terms "vessel" or "reaction vessel" comprise, but are not limited to, tubes, or the wells of plates such as microwell, deepwell or other types of multiwell plates, in which immobilization of the biological target material on the solid support takes place. The outer limits or walls of such vessels are chemically inert such that they do not interfere with the immobilization taking place within.

"Immobilize", in the context of the invention, means to capture objects such as the biological target material. Particularly, "immobilized on the solid support", means that the object or objects are associated with the solid support for the purpose of their separation from any surrounding media, and can be recovered e.g. by separation from the solid support material at a later point. In this context, "immobilization" can e.g. comprise the adsorption of nucleic acids to glass or other suitable surfaces of solid materials as described supra. Moreover, nucleic acids can be "immobilized" specifically by binding to capture oligonucleotides, wherein nucleic acids are bound by base-pairing to essentially complementary nucleic acids attached to a solid support. In the latter case, such specific immobilization leads to the predominant binding of target nucleic acids.

A "separation station" is a device or a component of an analytical system allowing for the isolation of the solid support from the other material present in the fluid sample. Such a separation station can e.g. comprise, while it is not limited to these components, a centrifuge, a rack with filter tubes, a magnet, or other suitable components. In some embodiments, the separation station comprises one or more magnets. In certain embodiments, one or more magnets are used for the separation of magnetic particles, such as e.g. magnetic glass particles, as a solid support. If, for example, the fluid sample and the solid support material are combined together in the wells of a multiwell plate, then one or more magnets comprised by the separation station can e.g. be contacted with the fluid sample itself by introducing the magnets into the wells, or said one or more magnets can be brought close to the outer walls of the wells in order to attract the magnetic particles and subsequently separate them from the surrounding liquid.

A "wash buffer" is a fluid that is designed to remove undesired components, especially in a purification procedure. Such buffers are well known in the art. In the context of the purification of the biological target material, the wash buffer is suited to wash the solid support material in order to separate the immobilized biological target material from any unwanted components. As described above, the washing buffer used in the context of the present invention comprises a cationic amine. The wash buffer may, for example, contain ethanol and/or chaotropic agents in a buffered solution. The washing buffer can also be a buffered solution without ethanol and/or chaotropic agents as described above. In some embodiments, the washing buffer has an acidic pH value. Also in some embodiments, the washing buffer consists of a buffered aqueous solution and a cationic amine. Often the washing solution or other solutions are provided as stock solutions which have to be diluted before use. A wash buffer, which in some embodiments is an aqueous buffer, comprises a buffering substance. Buffer substances are generally important for maintaining a certain pH value or pH range in a solution. This is the prerequisite for most biological systems, and mostly also desirable for in vitro reactions. Useful buffer substances in the context of the invention are citrate buffers such as sodium citrate, but also Tris (Tris-(hydroxymethyl)-aminomethane) buffers such as Tris HCl, phosphate, N-(2-hydroxyethyl)-piperazine-N'-(2-ethanesulfonic acid) (HEPES), acetate buffers, but also other buffer substances can be used in the context of the invention.

The washing in the process according to the invention requires a more or less intensive contact of the solid support and the biological target material immobilized thereon with the wash buffer. Different methods are possible to achieve this, e.g. incubation of a chromatographic column with the wash buffer, or in the case of binding particles such as e.g. beads, shaking the wash buffer with the solid support in or along with the respective vessel or vessels. Another advantageous method is aspirating and dispensing the suspension comprising wash buffer and solid support one or more times. This method is in some embodiments carried out using a pipet, wherein said pipet in some embodiments comprises a disposable pipet tip into which said suspension is aspirated and from which it is dispensed again.

A "cationic amine", in the context of the invention, means a compound comprising at least one positively charged nitrogen atom. Said positive charge can be e.g. due to protonation of ammonia or of a primary, secondary or tertiary amine, or due to alkylation of the amine to form a quaternary ammonium ion. In some embodiments of the invention, said cationic amine is added to the wash buffer as a salt, in certain embodiments as a salt of acetic acid, hydrochloric acid or citric acid.

In some embodiments, the positive charge relies on an appropriate pH value of the surrounding media. The person skilled in the art is familiar with measures to adjust the pH value in an appropriate manner to maintain the positive charge of the cationic amine.

The above-mentioned pH-dependent positive charge is the result of protonation in aqueous solution. More specifically, the cationic amine as used in the context of the present invention can acquire its positive charge via protonation of at least one of its nitrogen atoms. The person skilled in the art is aware of the circumstance that such protonation is an equilibrium function depending on the pH value as described above. In the context of the present invention, it is thus not required that all molecules of the amine in the wash buffer be protonated in order to achieve the desired technical effect.

In other embodiments, such as in the case of quaternary amines, said positive charge is practically independent of the pH value of the surrounding media.

An aspect of the invention is the method described above, wherein said cationic amine is a primary, secondary, tertiary or quaternary amine of the general Formula I,

Formula I wherein R1 and R2 can be, independently from each other, hydrogen, an cycloalkyl, aryl or heteroaryl residue, R3 can be hydrogen, an alkyl, cycloalkyl, aryl or heteroaryl residue, x is an integer from 1 to 12, R4 can be hydrogen or a residue according to the general Formula II,

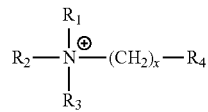

Formula II wherein R5 can be hydrogen, an alkyl, cycloalkyl, aryl or heteroaryl residue, R6 can be hydrogen, an alkyl, cycloalkyl, aryl or heteroaryl residue, or —(CH2)3-NH2, or —(CH2)4-NH—(CH2)3-NH2, and R7 can be hydrogen, an alkyl, cycloalkyl, aryl or heteroaryl residue. The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "aryl" denotes a monovalent aromatic carbocyclic mono- or bicyclic ring system comprising 6 to 10 carbon ring atoms. Examples of aryl moieties include phenyl and naphthyl.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

In some embodiments, said cationic amine is selected from the group of putrescine, ethylene diamine, cadaverine, spermidine, spermine, trimethylene diamine, and ammonium.

In some embodiments of the method described, said cationic amine is an alkylene diamine An "alkylene diamine" is an "alkyl" compound, as specified above substituted with two amino groups. In some embodiments, said amino groups are located at the respective ends of the linear hydrocarbon chains. In the context of the invention, an alkylene diamine can carry substituents e.g. as characterized by Formulae I and II, or it can be unsubstituted.

Unsubstituted alkylene diamines confer the advantage that the two terminal amino groups, in their protonated form, are sterically well-positioned to interact with the negatively charged moieties of undesired impurities like e.g. hemin.

In some embodiments, the alkylene diamine is selected from the group of ethylene diamine, putrescine and cadaverine.

Among the alkylene diamines; these compounds show particularly good results when used in the method described above. They are efficient in removing inhibitory impurities and do not interfere with downstream analysis.

As mentioned above, the biological target material is often isolated with the aim of subjecting it to analytical methods.

Hence, an aspect of the invention is the method described above, further comprising step
  e. Analyzing the isolated biological target material.

Such analysis can comprise e.g. nucleic acid analytics like PCR including realtime PCR or sequencing methods, or protein analytics such as e.g. antibody-based assays like ELISA or other methods. The analytics can also include methods for detection of the isolated biological material, such as e.g. chemi- or electroluminescence-based techniques, radiography or other detection methods. In some embodiments, the isolated biological target material is analyzed by amplification, in some embodiments by PCR, in further embodiments by realtime PCR.

The method described above is particularly useful in the context of nucleic acid isolation with possible subsequent analysis e.g. by PCR.

Thus, an aspect of the invention is the method described above, wherein the biological target material is a nucleic acid.

Another aspect of the invention is the use of a wash buffer comprising a cationic amine for selectively removing an inhibitor of the analysis of a biological target material from a solid support to which said biological target material is bound.

"Selectively removing", in the context of the invention, means removing the major part of an undesired compound from an object while other compounds largely remain bound to the latter. More specifically, it means removing the major part of an inhibitor of downstream analysis of a biological target material from a solid support to which said biological target material is bound. It is clear to a person skilled in the art that said selectivity is usually not quantitative, i.e. a minor part of the target material might be removed from the solid support along with the major part of the undesired impurities.

The use of a cationic amine in a wash buffer for removing impurities from a solid support is especially advantageous when isolating nucleic acids from a fluid sample.

Therefore, another aspect of the invention is the use described above, wherein the biological target material is a nucleic acid and the downstream analysis comprises or consists of nucleic acid amplification.

As set out above, analytical methods involving nucleic acid amplification such as e.g. PCR are often very sensitive to inhibition by impurities derived from fluid samples containing biological material, such that the method and the use described above are especially useful in this context.

Among possible fluid samples, whole blood is an especially complex matrix. Since e.g. hemin is abundant in whole blood, the method and the use described above are particularly useful in this context.

Thus, an aspect of the invention is the method or the use described above, wherein the fluid sample is whole blood.

In analogy to the method described further supra, an aspect of the invention is the use described above, wherein said cationic amine is a primary, secondary, tertiary or quaternary amine of the general Formula I,

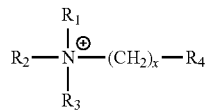

Formula I wherein $R_1$ and $R_2$ can be, independently from each other, hydrogen, an alkyl, cycloalkyl, aryl or heteroaryl residue, $R_3$ can be hydrogen, an alkyl, cycloalkyl, aryl or heteroaryl residue, x is an integer from 1 to 12, $R_4$ can be hydrogen or a residue according to the general Formula II,

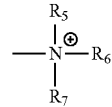

Formula II wherein $R_5$ can be hydrogen, an alkyl, cycloalkyl, aryl or heteroaryl residue, $R_6$ can be hydrogen, an alkyl, cycloalkyl, aryl or heteroaryl residue, or —(CH2)3-NH2, or —(CH2)4-NH—(CH2)3-NH2, and $R_7$ can be hydrogen, an alkyl, cycloalkyl, aryl or heteroaryl residue.

A further aspect of the invention is a kit for isolating a biological target material from a fluid sample, said kit comprising the components:
  a binding buffer
  a solid support
  a wash buffer comprising a cationic amine
  optionally an elution buffer,
wherein the binding buffer and the washing buffer are different buffers contained in different vessels.

In analogy to the method and the use described further supra, an aspect of the invention is the kit described above, wherein said cationic amine is a primary, secondary, tertiary or quaternary amine of the general Formula I,

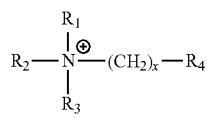

Formula I wherein $R_1$ and $R_2$ can be, independently from each other, hydrogen, an alkyl, cycloalkyl, aryl or heteroaryl residue, $R_3$ can be hydrogen, an alkyl, cycloalkyl, aryl or heteroaryl residue, x is an integer from 1 to 12, R4 can be hydrogen or a residue according to the general Formula II,

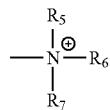

Formula II wherein R5 can be hydrogen, an alkyl, cycloalkyl, aryl or heteroaryl residue, R6 can be hydrogen, an alkyl, cycloalkyl, aryl or heteroaryl residue, or —(CH2)3-NH2, or —(CH2)4-NH—(CH2)3-NH2, and R7 can be hydrogen, an alkyl, cycloalkyl, aryl or heteroaryl residue.

Another aspect of the invention is the kit described above, wherein said binding buffer comprises a chaotropic agent
and/or
said solid support comprises silica and/or a magnetic material
and/or
said wash buffer comprising a cationic amine has a pH value below 7
and/or
said elution buffer is aqueous and/or comprises a preserving agent.

The solid support and the wash buffer comprising a cationic amine have been defined and described hereinabove.

A "binding buffer" is a liquid media that facilitates binding of the biological target material to the solid support. In some embodiments, the binding buffer also serves as a lysis buffer for disrupting cells or viral particles, thereby releasing the biological target material.

Chaotropic agents, which generally disturb the ordered structure of water molecules in solution and non-covalent binding forces in and between molecules, can make several contributions to the procedure of sample preparation. In particular, but not only, they can be applied as RNase inhibitors by disturbing the nuclease's tertiary structure. Usually, no further RNase inhibitor has to be applied to the lysis buffer when the biological target material is a nucleic acid. Besides, chaotropic agents contribute to the disruption of biological membranes, such as plasma membranes or the membranes of cell organelles if present. Also, they can play a significant role in the adhesive binding of nucleic acids to surfaces like glass. Useful chaotropic agents in the context of the invention are e.g. guanidinium salts like guanidinium thiocyanate or guanidinium hydrochloride or guanidinium chloride or guanidinium isothiocyanate, urea, perchlorates such as e.g. potassium perchlorate, other thiocyanates or potassium iodide.

The use of alcohol in a binding buffer can also be advantageous e.g. for nucleic acid preparation, as known by the person skilled in the art. Useful in the context of the invention is e.g. polidocanol, while other alcohols may also be used. The use of polidocanol for the preparation of nucleic acids has e.g. been described in EP 1 932 913.

Reducing agents can also contribute to the denaturation of undesired components such as e.g. degrading enzymes. In particular, reducing agents, as widely known in the art, cleave inter- and intramolecular disulfide bonds, which are especially important for the tertiary structure of many proteins. Useful in the context of the invention are reducing agents such as e.g. dithiothreitol (DTT), but other reducing agents known in the art such as e.g. 2-mercaptoethanol can also be employed.

An "elution buffer" in the context of the invention is a suitable liquid for separating the biological target material from the solid support. Such a liquid may e.g. be distilled water or aqueous salt solutions, such as e.g. Tris buffers like Tris HCl, or HEPES, or other suitable buffers known to the skilled artisan. The pH value of such an elution buffer is preferably alkaline or neutral. Said elution buffer may contain further components such as preserving agents like e.g. chelators like EDTA, which stabilizes the isolated biological target material, such as e.g. nucleic acids, by inactivation of degrading enzymes.

As mentioned in the context of the method and the use described above, in some embodiments of the kit described above the biological target material is a nucleic acid. Also in some embodiments of the kit described above, the fluid sample is whole blood.

Embodiments of the present invention will be further described in the following examples, which do not limit the scope of the invention described in the claims.

EXAMPLES

The following examples and figures are provided to aid the understanding of the present invention, the true scope of which is set forth in the appended claims. It is understood that modifications can be made in the procedures set forth without departing from the spirit of the invention.

Example I

Test of Amine Compounds for the Selective Preparation of Biological Samples

Experimental Design

In order to obtain an accurate measure of the efficiency of experimental sample prep processes, a method to simultaneously amplify and detect 2 synthetic targets was devised. These targets are introduced into the sample prep/amplification/detection workstream at different points in the process, whereby a Full Process Control (FPC) is introduced into a sample matrix and an Inhibition Control (IC) is introduced into the PCR Master Mix. The detection of the FPC is influenced by the efficiency with which this target is recovered through the sample prep process compounded with the effect of PCR inhibitors on the amplification and detection of this target. The IC does not go through the sample prep process, so the amplification and detection of this material is influenced only by the presence of PCR inhibition. In this way, the effect of changing sample preparation process elements, (e.g. nucleic acid type, sample matrix, process and reagent combinations) on the recovery of nucleic acids can be evaluated and differentiated from the effect of PCR inhibition. The 2 targets should be amplified and detected with similar efficiencies, and they should be influenced by inhibitors to substantially the same extent, in order for this experimental design to be valid.

From a diagnostic perspective both DNA and RNA forms of nucleic acids are suitable for study. It is therefore advantageous to construct the synthetic targets for this experimental framework in both of these forms. In order to normalize for the variation of amplification efficiencies of different targets, the nucleic acid sequence of the amplicons should be the same for both forms of each of the targets. However, since they are introduced into the processes under different conditions, they do need to be configured in different forms. The DNA FPC can be introduced into the sample Matrix in 2 forms, as plasmid DNA or as an encapsulated, phage λ DNA construct. This latter more closely mimics a protein coated DNA virus particle, for example, than would the plasmid. The phage λ particle requires lysis in order to release the encapsulated DNA suitable for capture on a silica surface. The corresponding IC for this DNA target should also be DNA in form, but since this is introduced post lysis, this should be in the form of a plasmid. Analogously, for RNA, the FPC is preferably an armored RNA construct, and the IC is an RNA transcript.

In order to obtain a more complete analysis of the eluate derived from any sample prep process, it is advisable to chemically analyze the eluates, to measure any changes in the chemical composition of the eluate brought about by the process change under study. Specific methods to identify and quantitate specific inhibitors of the PCR process were developed. The isolation of nucleic acids from complex sample specimens can lead to eluates in which PCR performance is very poor due to the co-purification of possible PCR inhibitors along with the desired nucleic acids. It was observed that by processing whole blood with standard sample prep reagents, a reddish eluate can be obtained suggesting the presence of iron-containing molecules such as hemoglobin or hemin. It was important to establish analytic methods to detect and quantify such inhibitors. Other examples of known PCR inhibitors such as bilirubin, humic acid or melanin (as would be obtained from melanoma tissue samples) were candidates for eluate analysis and suitable analytic methods for these were developed.

Two experimental methods were implemented for the evaluation of inhibitor removal from sample prep workflows. In order to screen potential wash buffers for their ability to remove inhibitors, model systems were devised, in which known inhibitors were added to human plasma and this spiked plasma was used in evaluations of sample prep workflows. In this way many combinations of wash buffers could be examined, along with several different known inhibitors. The second type of experiment used whole blood as a sample input. This experiment was used to verify the performance of the candidate wash buffers discovered through the screening process above.

Experimental Setup

Samples underwent fully automated sample preparation on a modified Hamilton STAR instrument and subsequent amplification/detection on a LightCycler 480 (Roche Diagnostics GmbH, Mannheim/DE). The specimen process volume of 850 µL was constant for all sample matrices tested. EDTA plasma and serum specimen input volume 850 of µL was implemented. Fresh whole blood specimen (resp. cadaveric specimen) input volume of 150 µL (resp. 100 µL) was diluted with 700 µL (resp. 750 µL) specimen diluent to reach the total process volume of 850 µL.

Sample Preparation

Samples underwent fully automated sample preparation on a modified Hamilton STAR instrument (compare WO 2012/013733). The principle of sample preparation can be described in four major steps:

Sample assembly

Lysis and binding

Wash

Elution

The following chapters describe the single steps in further detail.

Sequence of Sample Preparation

Sample Assembling Step

The biological sample to be tested (volume depending on sample matrix) is, if needed, diluted with specimen diluent to reach a final process volume of 850 µL. A total volume of 50 µL of FPC Reagent is added, followed by 50 µL of protease reagents. To this mixture 100 µL of Magnetic Glass Particle (MGP) Reagent are added (compare WO 96/41811; Magnetic Pigments).

Lysis/Binding Step

To the assembled sample 1250 µL of lysis buffer are added and the lysis binding reaction is carried out at 40° C. for 10 min at constant mixing allowing cell lysis and binding of nucleic acids to the magnetic glass particles. A magnetic field is applied to allow magnetic separation of MGP-bound nucleic acids from surrounding liquids. MGP-surrounding lysis solution is removed and magnetic field released.

Wash Step

In an initial wash step, a total volume of 900 µL wash buffer is added followed by mixing. An additional volume of 1500 µL of wash buffer is added and followed by mixing. A magnetic field is applied to allow magnetic separation of MGP-bound nucleic acids from surrounding liquids. The wash solution is removed and the magnetic field released. In a second wash step, a total volume of 2000 µL is added followed by mixing. A magnetic field is applied to allow magnetic separation of MGP-bound nucleic acids from surrounding liquids. The wash solution is removed and the magnetic field released.

Elution Step

A total volume of 50 µL of elution buffer is added and nucleic acids are eluted from MGP with repeated mixing for 6 min at 80° C. A final volume of 25 µL of eluate is used for PCR assembly.

Reagents of Sample Preparation

| | Concentration |
|---|---|
| Specimen Diluent | |
| Tris, pH 7.4 | 5 mM |
| Methylparaben | 0.1% (w/v) |
| Sodium Azide | 0.095% (w/v) |
| FPC Reagent | |
| Tris, pH 8.0 | 10 mM |
| EDTA | 0.1 mM |
| Sodium Azide | 0.05% (w/v) |
| Poly (rA) RNA | 20 mg/L |
| FPC DNA (resp. RNA) | 2 copies/µL |
| | (6 copies/µL) |
| Protease Reagent | |
| Tris, pH 5.5 | 10 mM |
| EDTA | 1 mM |
| Calcium Chloride | 5 mM |
| Calcium Acetate | 5 mM |
| Glycerol | 50% (w/v) |
| Protease | 80 mg/mL |
| MGP Reagent | |
| Tris, pH 8.5 | 30 mM |
| Methylparaben | 0.1% (w/v) |
| Sodium Azide | 0.095% (w/v) |
| MGP Powder | 60 mg/mL |
| Lysis buffer | |
| DTT | 2% (w/v) |
| Polidocanol | 5% (w/v) |
| Guanidine Thiocyanate | 4M |
| Sodium Citrate, pH 5.8 | 50 mM |

-continued

|  | Concentration |
|---|---|
| Wash buffer (best mode) | |
| Putrescine dihydrochloride ≥98.0% (Sigma Aldrich) | 22 mM |
| Sodium Citrate | 7.5 mM |
| Methylparaben | 0.1% (w/v) |
| NaOH, 1M, (Sigma Aldrich) | To bring pH to 4.1 |
| Elution buffer | |
| Tris, pH 8.5 | 5 mM |
| Methylparaben | 0.2% (w/v) |

Additional Examples of Wash Buffers

In addition to the above described (best mode) putrescine-containing wash buffer, several amine-containing wash buffers have been successfully applied (data not shown) in the sample preparation procedure described herein. Putrescine can be replaced by the following amines:

| Amine candidates for inhibitor removal in wash buffer | Concentration |
|---|---|
| Ethylene diamine dihydrochloride | 26 mM |
| Ethylene diamine diacetate | 26 mM |
| Spermidine dihydrochloride | 22 mM |
| Cadaverine dihydrochloride | 26 mM |
| Spermine dihydrochloride | 22 mM |
| Ammonium Acetate | 52 mM |
| Trimethylenediamine dihydrochloride | 26 mM |

PCR Assay
PCR Assembly

A total volume of 25 μL of eluate is transferred to a 96-microwell plate. The PCR reaction volume of 50 μL, is assembled as follows:

| PCR reaction component | Volume |
|---|---|
| Eluate | 25 μL |
| MMx R1 | 5 μL |
| MMx R2 | 15 μL |
| IC2 reagent | 5 μL |

|  | Concentration |
|---|---|
| IC Reagent | |
| Tris, pH 8.0 | 10 mM |
| EDTA | 0.1 mM |
| Sodium Azide | 0.05% (w/v) |
| Poly (rA) RNA | 20 mg/L |
| IC DNA (resp. RNA) | 50 copies/μL (80 copies/μL) |
| MMx R1 (in H₂O) | |
| Mn(Ac)₂ * 4H₂O (pH 6.1 adjusted with acetic acid) | 50 mM |
| NaN₃, buffered with 10 mM Tris at pH 7 | 0.36 μM |
| MMx R2 (in H₂O) | |
| DMSO (%) | 13.33 μM |
| NaN₃, buffered with 10 mM Tris at pH 7 | 0.09 μM |
| KOAc (pH 7.0) | 366.667 mM |
| Glycerol (%) | 13.33 μM |
| Tricine pH 8.0 | 166.667 mM |
| NTQ21-46A - Aptamer | 0.741 μM |
| UNG (U/uL) | 0.67 μM |
| Igepal (stock solution pre-warmed at 37° C.) (%) | 0.08 μM |
| dGTP | 1.667 mM |
| dATP | 1.667 mM |
| dCTP | 1.667 mM |
| dUTP | 3.333 mM |
| ZO5-D Polymerase (U/μl) | 2 μM |
| SEQ ID NO. 1 | 0.5 μM |
| SEQ ID NO. 2 | 0.5 μM |
| SEQ ID NO. 3 | 0.5 μM |
| SEQ ID NO. 4 | 0.5 μM |
| SEQ ID NO. 5 | 0.333 μM |
| SEQ ID NO. 6 | 0.333 μM |

Amplification and Detection

For amplification and detection, the microwell plate was manually sealed and transferred to a LightCycler 480. The following PCR profile was used:

|  | Cycles | Target (° C.) | Hold (hh:mm:ss) | Ramp |
|---|---|---|---|---|
| Pre-PCR | 1 | 50 | 00:02:00 | 4.4 |
|  |  | 94 | 00:00:05 | 4.4 |
|  |  | 55 | 00:02:00 | 2.2 |
|  |  | 60 | 00:06:00 | 4.4 |
|  |  | 65 | 00:04:00 | 4.4 |
| 1. Meas | 5 | 95 | 00:00:05 | 4.4 |
|  |  | 55 | 00:00:30 | 2.2 |
| 2. Meas | 45 | 91 | 00:00:05 | 4.4 |
|  |  | 58 | 00:00:25 | 2.2 |
| Post | 1 | 40 | 00:02:00 | 2.2 |

Synthetic Targets

The synthetic targets (FPC and IC) consist of linearized plasmid DNA particles or RNA transcripts. Nucleic acid particles are used at pre-defined copy numbers per reaction.

The general design concept for these targets consists of a common nucleic acid sequence which will be either RNA or DNA, and will be armored as such in particles termed Armored RNA (MS2 phage coat protein particles) or Armored DNA (lambda phage particles). Each target will have a corresponding set of specific primers and differentially fluorescently labeled TaqMan probes to be used in all assays, thus removing the target type-dependent influence on estimation of sample prep efficiency. To this end, each target, along with its corresponding primers and probes, was designed using the NCBI Blast program and EMBOSS shuffleseq (European Molecular Biology Open Software Suite) to generate a unique sequence. The FPC probe was labeled with CY5 and the IC probe was labeled with HEX dye. The constructs were designed and cloned for further evaluation. To produce armored RNA the sequence was cloned into the vector pCP-1. To produce transcript the sequence was cloned into pSP64a. To produce armored DNA the sequence was cloned into lambda GT11.

| Internal Control | Copy numbers (cp) per reaction (rxn) |
|---|---|
| IC DNA (resp. RNA) | 100 cp/rxn (300 cp/rxn) |
| FPC DNA (resp. RNA) | 250 cp/rxn (400 copies/μL) |

DNA: Linearized Plasmid

A recombinant plasmid was constructed using the poly(A) cloning vector pSP64a (Promega) was linearized with restriction enzyme EcoRI.

Region of Interest Recombinant Plasmid pEF054 (FPC)

Sequence of interest of recombinant plasmid pEF054 linearized with restriction enzyme EcoRI IC in poly(A) cloning vector pSP64a (after bp 270) corresponds to SEQ ID NO. 7:

Recombinant Plasmid pEF066 (IC)

Sequence of interest of recombinant plasmid pEF066 linearized with restriction enzyme EcoRI IC in poly(A) cloning vector pSP64a (after bp 503) corresponds to SEQ ID NO. 8.

Eluate Chemical Analysis (ISS)

During the experiments where different wash buffers were screened, a way of monitoring the effectiveness of inhibitor removal was developed. Candidate PCR inhibitors were analyzed in the eluates obtained with the sample preparation process described previously. The removal of these specific inhibitors was used to monitor the efficiency of the wash buffers. Their PCR inhibitory properties were evaluated by spiking them directly into the PCR and observing the PCR response with different concentrations of the respective compounds. For the experiments where whole blood was processed, hemin was the inhibitor of choice. To test if the added amine in the wash buffer can be used with other difficult sample specimens, these latter were simulated by the addition of melanin, bile salts and humic acid to human plasma in the sample prep process. Analytical methods were developed to enable the relative quantitation of the specific compounds in the eluates.

Hemin Detection (ISS)

The HPLC-based detection of hemin was carried out at 20° C. on an Agilent 1100 liquid chromatography apparatus coupled with an Agilent PDA Detector. The measurement was carried out using 3D absorbance spectrum collection between 200 and 800 nm and the output was given by single wave detection at both $\lambda$=254 and 400 nm. The eluate samples were centrifuged for 3 min at 4000 rpm and 25° C. and the supernatant used for the analysis. A 30 µL sample of the eluate was injected and separated on a 5 µm 100 Å 4.1×100 mm Hamilton PRP-1 polymeric HPLC column. All the mobile phases were prepared with HPLC grade compounds provided by Sigma Aldrich. Mobile phase (A) was prepared adding $CF_3COOH$ (0.1% v/v) to Milli-Q filtered water. This latter was added in order to suppress peptide ionization. Mobile phase (B) was chromatographic grade acetonitrile. The HPLC analysis was operated in a constant flow mode and the flow rate was kept at 1 mL/min. The results of the chromatographic analysis were processed by the Agilent Chemstation Modular 3D Software and were as follows when using a wash buffer containing putrescine as a cationic amine:

TABLE 1

The area of the hemin peak at 17.7 min in eluate produced with and without putrescine

| Sample | Area of the hemin peak using wash buffer (see above) without cationic amine (3 replicates) | Area of the hemin peak using wash buffer (see above) containing putrescine dihydrochloride (3 replicates) |
|---|---|---|
| 100 µL whole blood aged 24 h | Average: 30.88 STDEV: 1.78 | average: 3.56 STDEV: 0.55 |
| 100 µL whole blood aged 48 h | Average: 43.74 STDEV: 4.16 | average: 2.92 STDEV: 0.19 |

The gradient used during the separation was:

| Time/min | (A) | (B) |
|---|---|---|
| 0-5 | 100 | 0 |
| 5-10 | 90 | 10 |
| 10-15 | 50 | 50 |
| 15-20 | 0 | 100 |

The identification of the hemin compound from the eluate of whole blood was confirmed by HPLC analysis of an authentic sample of hemin (BioXtra, porcine, ≥98.0% (HPLC) Sigma Aldrich, Mat Nr 51280) which gave identical HPLC retention times and UV absorbance spectra.

Bilirubin Detection (ISS)

The detection of bilirubin was carried out on an HPLC system as described above.

The gradient used during the separation was:

| Time/min | (A) | (B) |
|---|---|---|
| 0-5 | 100 | 0 |
| 5-15 | 0 | 100 |
| 15-30 | 0 | 100 |
| 30-31 | 50 | 50 |
| 31-32 | 100 | 0 |
| 32-40 | 100 | 0 |

The identification of the bilirubin compound was carried out using commercially available bilirubin (≥98.0% Sigma Aldrich, Mat Nr B4126). The results were comparable to the ones obtained for the detection of hemin.

Melanin Detection (ISS)

Melanin was detected by absorbance measurements at $\lambda$=562 nm using a multiwell plate reader (Tecan Infinity 500).

For the quantitation of melanin, linearity of response was established ($R^2$=0.9998). The absorbance of melanin solutions between 7.8 and 500 ppm, was measured with using commercially available synthetic melanin (Sigma Aldrich, Mat Nr M8631) dissolved in elution buffer (5 mM Tris buffer, 0.2% (w/v) methylparaben, pH 8.5) and using an eluate produced with 0 ppm melanin as a blank sample (100 µL). The results were comparable to the ones obtained for the detection of hemin. The following parameters were used for the analyses:

| | |
|---|---|
| Multiple Reads per Well (Circle (filled)) | 4 × 4 |
| Multiple Reads per Well (Border) | 1350 µm |
| Wavelength | 562 nm |
| Bandwidth | 5 nm |
| Number of Flashes | 10 |
| Settle Time | 1 ms |

Example II

Test of a Putrescine-Containing Wash Buffer for the Preparation of Stool Samples In the series of experiments with an assay targeting *Clostridium difficile* described herein, it was shown that PCR inhibition by intrinsic inhibitors contained in the sample material (stool) could be reduced by introducing putrescine in the wash buffer used in the first step for washing magnetic glass particles (MGP). A higher stool input volume was tolerated while using a putrescine-containing wash buffer, leading to improved assay sensitivity.

Experimental Setup

Unless otherwise indicated, the instruments and workflow were as described for Example 1. The MGPs were washed twice as above, while the putrescine-containing wash buffer was employed in the first wash step.

1) Inhibitory Stool Tolerance with Variable Sample Input Volume

Method

Pooled *C. difficile* positive (determined by the commercially available Cepheid Xpert® *C. difficile*/Epi Assay) inhibitory stool samples were used in the study. Two stool sampling devices (inoculation loop and flocked swab) were used to transfer stool into Cobas® PCR media (Roche Diagnostics, Cat. No. 06466281190). When using a 10 µl inoculation loop as stool transfer device, the maximum allowed input volume of stool suspension (400 µL) was used to compensate for a very low amount of primary specimen. When using a flocked swab which transfers much larger amounts of primary specimen, various volumes of stool suspension were evaluated to find the upper tolerance limit. Table 2 shows the conditions that were tested in this study. An Internal Control (IC) was included in each sample tested.

TABLE 2

Experimental Design for inhibitory stool tolerance, N = 8

| Sampling Device | Stool suspension input Volume (µL) | Putrescine in Wash Buffer | Stool in Each Sample Extraction (µL) |
|---|---|---|---|
| Inoculation loop | 400 | No | 0.9 |
| Inoculation loop | 400 | Yes | 0.9 |
| Flocked swab | 75 | No | 2.6 |
| Flocked swab | 100 | No | 3.5 |
| Flocked swab | 150 | No | 5.2 |
| Flocked swab | 200 | No | 7.0 |
| Flocked swab | 75 | Yes | 2.6 |
| Flocked swab | 150 | Yes | 5.2 |
| Flocked swab | 200 | Yes | 7.0 |

Result

Figure 2:
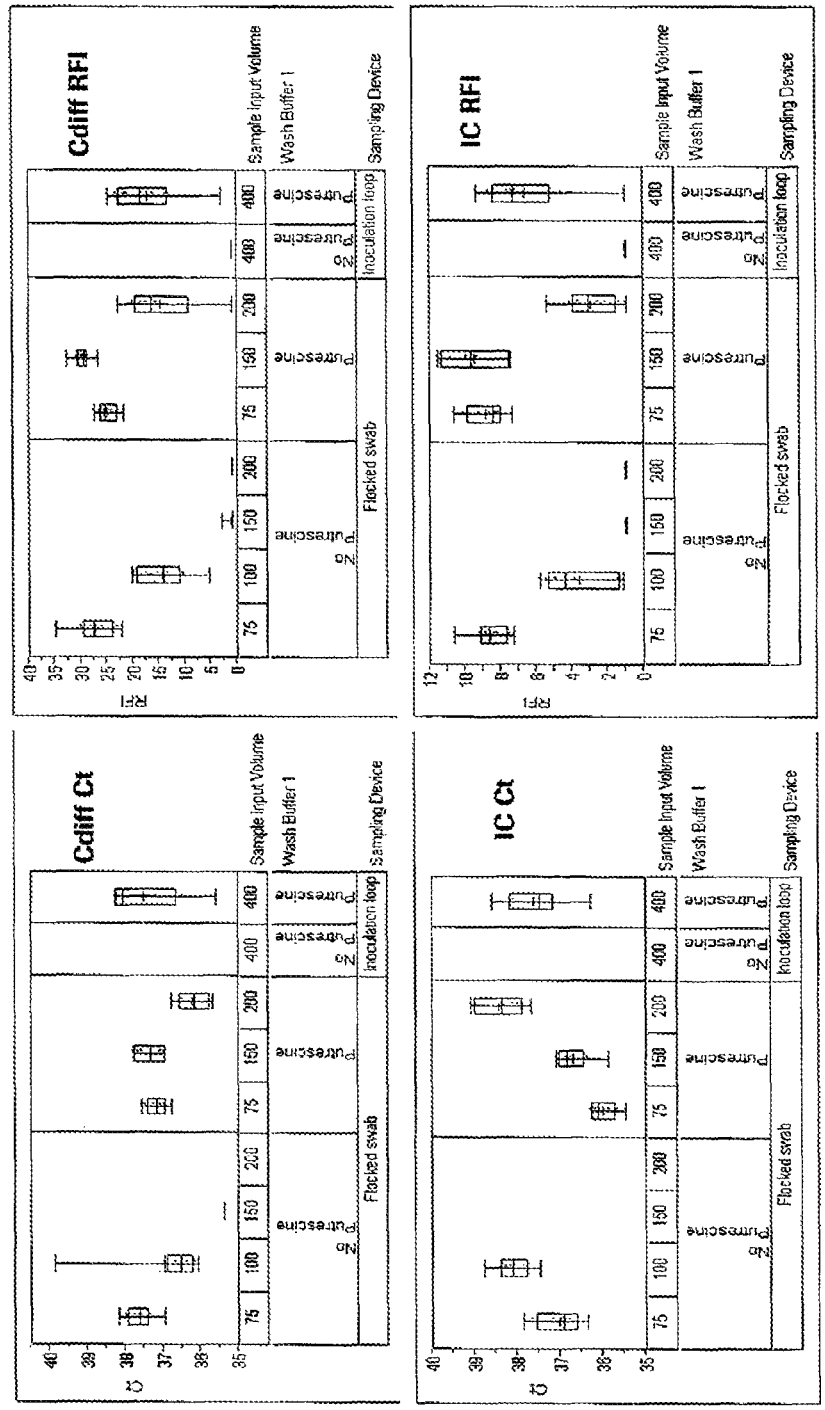
FIG. 2 shows inhibitory stool tolerance as function of processing volume with different sampling devices. With putrescine in the wash buffer, the inhibitory stool tolerance increased with an acceptable fluorescent signal (RFI) and Ct values.

Results from this study are summarized in FIG. 2. When using flocked swabs for stool sampling, most replicates showed no fluorescent signal at 150 µL input without putrescine in the wash buffer, indicating inhibition. With putrescine, the inhibitory stool tolerance increased with an acceptable fluorescent signal and Ct values observed with up to 200 µL stool suspension input. When using an inoculation loop for stool transfer (400 µL stool suspension input volume), the signal was completely inhibited without putrescine in the wash buffer. Inhibition was removed by adding putrescine to the wash buffer.

Conclusions

Putrescine in the MGP wash buffer allows for higher stool input, therefore potentially increasing the assay sensitivity.

The best balance between target signal and degree of inhibition appears to be achieved with 150 µL stool suspension input with putrescine-containing wash buffer when using flocked swabs as stool transfer device (see FIG. 2)

2) Analytical Sensitivity Comparison with Variable Sample Input Volume

Method

Analytical sensitivity of the above-mentioned assay was assessed with four combinations of stool sampling devices and stool suspension processing volumes as described in Table 3. *C. difficile* positive (determined by the commercially available Cepheid Xpert® *C. difficile*/Epi Assay) specimen was serially diluted to 7 levels into a pool of non-inhibitory negative specimens. Each dilution level was tested in 24 replicates for each condition. Probit analysis was used to determine the limit of detection (LoD).

TABLE 3

Conditions Tested for Assay Analytical Sensitivity

| Sampling Device | Processing Volume (µL) | Putrescine in Wash Buffer |
|---|---|---|
| Inoculation loop | 400 | No |
| Inoculation loop | 400 | Yes |
| Flocked swab | 75 | No |
| Flocked swab | 150 | Yes |

Result

The results from this study are summarized in Table 4. The best condition for tolerating inhibition from study 1 (flocked swab stool sampling with 150 µL input and putrescine in wash buffer, see above) also showed best sensitivity.

TABLE 4

Analytical Sensitivity Comparison under Different Conditions

| Sampling Device | Processing Volume (µL) | Putrescine in Wash Buffer | Probit LoD Relative Concentration* | LoD 95% fiducial CI Lower | Upper |
|---|---|---|---|---|---|
| Inoculation loop | 400 | No | 7.5 | 5.0 | 12.2 |
| Inoculation loop | 400 | Yes | 5.6 | 3.7 | 9.0 |
| Flocked swab | 75 | No | 3.5 | 2.3 | 5.6 |
| Flocked swab | 150 | Yes | 1.0 | 0.6 | 1.6 |

*Lowest detectable level is set to 1.0 for this comparison

Conclusion

Results from this study confirmed that inhibitor removal from stool specimens by putrescine allows for more stool input, therefore increasing the assay sensitivity.

3) Comparison to the Cepheid Xpert® *C. difficile*/Epi Assay, Toxigenic and Reference *C. difficile* Culture Method Clinical specimens were collected at healthcare facilities in the US. Specimens were tested using the test mentioned above and results were compared to the Cepheid Xpert® *C. difficile*/Epi Assay and reference culture results. For the *C. difficile* assay, four conditions were tested for each stool specimen (see Table 5). A polyester swab was utilized as stool transfer device.

TABLE 5

Conditions tested using Individual Clinical Stool Specimens

| Sampling Device | Processing Volume (µL) | Putrescine in Wash Buffer |
|---|---|---|
| Flocked swab | 75 | No |
| Flocked swab | 150 | Yes |
| Polyester swab | 75 | No |
| Polyester swab | 150 | Yes |

Results

Results are summarized in Table 6 and Table 7. Table 6 shows the performance comparison to the Cepheid Xpert® *C. difficile*/Epi Assay and Table 7 shows the performance comparison to a reference culture (combination of direct and enriched colony isolation of toxigenic *C. difficile*). Results shown as "CDiff Invalid" indicate inhibition. Positive percent agreement to Cepheid Xpert® *C. difficile*/Epi Assay and sensitivity when using reference *C. difficile* culture as a standard improved slightly with the increase in stool suspension volume and use of putrescine containing wash buffer.

TABLE 6

Test performance compared to Cepheid Xpert® *C. difficile*/Epi Assay

| Cepheid Cdiff Test result | Cdiff Test result | Flocked swab | | Polyester swab | |
|---|---|---|---|---|---|
| | | 75 μL No putrescine | 150 μL With putrescine | 75 μL No putrescine | 150 μL With putrescine |
| Negative | Cdiff Invalid | 6 | 5 | 10 | 6 |
| | Cdiff NEG | 327 | 290 | 258 | 263 |
| | Cdiff POS | 1 | 4 | 4 | 3 |
| Positive | Cdiff Invalid | 0 | 0 | 0 | 2 |
| | Cdiff NEG | 6 | 5 | 7 | 5 |
| | Cdiff POS | 59 | 54 | 46 | 46 |
| Total sample tested | | 399 | 358 | 325 | 325 |
| Sensitivity | | 90.8% | 91.5% | 86.8% | 90.2% |
| Specificity | | 99.7% | 98.6% | 98.5% | 98.9% |
| Inhibition rate | | 1.5% | 1.4% | 3.1% | 2.5% |

TABLE 7

Test performance compared to *C. difficile* Reference Culture

| Cdiff Culture result | Cdiff Test result | Flocked Swab | | Polyester Swab | |
|---|---|---|---|---|---|
| | | 75 μL No putrescine | 150 μL With putrescine | 75 μL No putrescine | 150 μL With putrescine |
| Negative | Cdiff Invalid | 0 | 0 | 4 | 2 |
| | Cdiff NEG | 161 | 138 | 125 | 127 |
| | Cdiff POS | 2 | 2 | 2 | 3 |
| Positive | Cdiff Invalid | 0 | 0 | 0 | 0 |
| | Cdiff NEG | 6 | 4 | 3 | 4 |
| | Cdiff POS | 28 | 28 | 23 | 22 |
| Total sample tested | | 197 | 172 | 157 | 158 |
| Sensitivity | | 82.4% | 87.5% | 88.5% | 84.6% |
| Specificity | | 98.8% | 98.6% | 98.4% | 97.7% |
| Inhibition rate | | 0% | 0% | 2.5% | 1.3% |

Summary

Data from these studies demonstrated that a putrescine-containing wash buffer reduces PCR inhibition and increases analytical sensitivity While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method for isolating a biological target material from a fluid sample, said method comprising the steps:
   a. combining together a solid support and said fluid sample in a reaction vessel for a period of time and under conditions sufficient to permit said biological target material to be immobilized on the solid support,
   b. isolating the solid support material from the other material present in the fluid sample in a separation station,
   c. purifying the biological material by separating the fluid sample from the solid support material,
   d. washing the solid support material one or more times with a wash buffer comprising alkaline diamine selected from the group consisting of ethylene diamine, putrescine, and cadaverine.

2. The method of claim 1, further comprising step
   e. analyzing the isolated biological target material.

3. The method of claim 1, wherein the biological target material is a nucleic acid.

4. The method of claim 1, wherein the fluid sample is whole blood or blood plasma.

5. The method of claim 1, wherein the alkaline diamine is ethylene diamine.

6. The method of claim 1, wherein the alkaline diamine is putrescine.

7. The method of claim 1, wherein the alkaline diamine is cadaverine.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Primer/probe

<400> SEQUENCE: 1
ttgatagcaa tcggctatcg acta                                          24

<210> SEQ ID NO 2
<211> LENGTH: 27
<212> TYPE: DNA
<213> ORGANISM: Artificial Sequence
<220> FEATURE:
<223> OTHER INFORMATION: Primer/probe

<400> SEQUENCE: 2
gcttcgatac tcagtcatct cggtata                                       27

<210> SEQ ID NO 3
<211> LENGTH: 26
<212> TYPE: DNA
<213> ORGANISM: Artificial Sequence
<220> FEATURE:
<223> OTHER INFORMATION: Primer/probe

<400> SEQUENCE: 3

```
gggcgaatga tgcaggcttc agaatt                                          26
```

<210> SEQ ID NO 4
<211> LENGTH: 26
<212> TYPE: DNA
<213> ORGANISM: Artificial Sequence
<220> FEATURE:
<223> OTHER INFORMATION: Primer/probe

<400> SEQUENCE: 4

```
gttttctagc gttcgcccac ttcatt                                          26
```

<210> SEQ ID NO 5
<211> LENGTH: 27
<212> TYPE: DNA
<213> ORGANISM: Artificial Sequence
<220> FEATURE:
<223> OTHER INFORMATION: Primer/probe

<400> SEQUENCE: 5

```
tctctcgcca tctcctaccg cattggc                                         27
```

<210> SEQ ID NO 6
<211> LENGTH: 31
<212> TYPE: DNA
<213> ORGANISM: Artificial Sequence
<220> FEATURE:
<223> OTHER INFORMATION: Primer/probe

<400> SEQUENCE: 6

```
cggtggacga cagacaattt tacgattttg g                                    31
```

<210> SEQ ID NO 7
<211> LENGTH: 3221
<212> TYPE: DNA
<213> ORGANISM: Artificial Sequence
<220> FEATURE:
<223> OTHER INFORMATION: Control nucleic acid

<400> SEQUENCE: 7

```
aattcgtaat catgtcatag ctgtttcctg tgtgaaattg ttatccgctc acaattccac     60
acaacatacg agccggaagc ataaagtgta aagcctgggg tgcctaatga gtgagctaac    120
tcacattaat tgcgttgcgc tcactgcccg ctttccagtc gggaaacctg tcgtgccagc    180
tgcattaatg aatcggccaa cgcgcgggga gaggcggttt gcgtattggg cgctcttccg    240
cttcctcgct cactgactcg ctgcgctcgg tcgttcggct gcggcgagcg gtatcagctc    300
actcaaaggc ggtaatacgg ttatccacag aatcagggga taacgcagga aagaacatgt    360
gagcaaaagg ccagcaaaag gccaggaacc gtaaaaaggc cgcgttgctg gcgttttttcc   420
ataggctccg cccccctgac gagcatcaca aaaatcgacg ctcaagtcag aggtggcgaa    480
acccgacagg actataaaga taccaggcgt ttccccctgg aagctccctc gtgcgctctc    540
ctgttccgac cctgccgctt accggatacc tgtccgcctt tctcccttcg ggaagcgtgg    600
cgctttctca tagctcacgc tgtaggtatc tcagttcggt gtaggtcgtt cgctccaagc    660
tgggctgtgt gcacgaaccc cccgttcagc ccgaccgctg cgccttatcc ggtaactatc    720
gtcttgagtc caacccggta agacacgact tatcgccact ggcagcagcc actggtaaca    780
ggattagcag agcgaggtat gtaggcggtg ctacagagtt cttgaagtgg tggcctaact    840
acggctacac tagaagaaca gtatttggta tctgcgctct gctgaagcca gttaccttcg    900
gaaaaagagt tggtagctct tgatccggca aacaaaccac cgctggtagc ggtggttttt    960
```

```
ttgtttgcaa gcagcagatt acgcgcagaa aaaaggatc tcaagaagat cctttgatct      1020
tttctacggg gtctgacgct cagtggaacg aaaactcacg ttaagggatt ttggtcatga      1080
gattatcaaa aaggatcttc acctagatcc ttttaaatta aaaatgaagt tttaaatcaa      1140
tctaaagtat atatgagtaa acttggtctg acagttacca atgcttaatc agtgaggcac      1200
ctatctcagc gatctgtcta tttcgttcat ccatagttgc ctgactcccc gtcgtgtaga      1260
taactacgat acgggagggc ttaccatctg gccccagtgc tgcaatgata ccgcgagacc      1320
cacgctcacc ggctccagat ttatcagcaa taaaccagcc agccggaagg gccgagcgca      1380
gaagtggtcc tgcaaacttta tccgcctcca tccagtctat taattgttgc cgggaagcta      1440
gagtaagtag ttcgccagtt aatagtttgc gcaacgttgt tgccattgct acaggcatcg      1500
tggtgtcacg ctcgtcgttt ggtatggctt cattcagctc cggttcccaa cgatcaaggc      1560
gagttacatg atcccccatg ttgtgcaaaa aagcggttag ctccttcggt cctccgatcg      1620
ttgtcagaag taagttggcc gcagtgttat cactcatggt tatggcagca ctgcataatt      1680
ctcttactgt catgccatcc gtaagatgct tttctgtgac tggtgagtac tcaaccaagt      1740
cattctgaga atagtgtatg cggcgaccga gttgctcttg cccggcgtca atacgggata      1800
ataccgcgcc acatagcaga actttaaaag tgctcatcat tggaaaacgt tcttcggggc      1860
gaaaactctc aaggatctta ccgctgttga gatccagttc gatgtaaccc actcgtgcac      1920
ccaactgatc ttcagcatct tttactttca ccagcgtttc tgggtgagca aaaacaggaa      1980
ggcaaaatgc cgcaaaaaag ggaataaggg cgacacggaa atgttgaata ctcatactct      2040
tcctttttca atattattga agcatttatc agggttattg tctcatgagc ggatacatat      2100
ttgaatgtat ttagaaaaat aaacaaatag gggttccgcg cacatttccc cgaaaagtgc      2160
cacctgacgt ctaagaaacc attattatca tgacattaac ctataaaaat aggcgtatca      2220
cgaggccctt tcgtctcgcg cgtttcggtg atgacggtga aaacctctga cacatgcagc      2280
tcccggagac ggtcacagct tgtctgtaag cggatgccgg gagcagacaa gcccgtcagg      2340
gcgcgtcagc gggtgttggc gggtgtcggg gctggcttaa ctatgcggca tcagagcaga      2400
ttgtactgag agtgcaccat tcgacgctct cccttatgcg actcctgcat taggaagcag      2460
cccagtagta ggttgaggcc gttgagcacc gccgccgcaa ggaatggtgc atgcaaggag      2520
atggcgccca acagtccccc ggccacgggg cctgccacca tacccacgcc gaaacaagcg      2580
ctcatgagcc cgaagtggcg agcccgatct tccccatcgg tgatgtcggc gatataggcg      2640
ccagcaaccg cacctgtggc gccggtgatg ccggccacga tgcgtccggc gtagaggatc      2700
tggctagcga tgaccctgct gattggttcg ctgaccattt ccgggtgcgg acggcgtta       2760 ccagaaactc agaaggttcg tccaaccaaa ccgactctga cggcagttta cgagagagat      2820
gatagggtct gcttcagtaa gccagatgct acacaattag gcttgtacat attgtcgtta      2880
gaacgcggac acaattaata cataacctta tgtatcatac atacgattt aggtgacac       2940 tatagaatac aagctttgcc tgcttgatag caatcggcta tcgactaatg actgtcctgg      3000
cggtctctcg ccatctccta ccgcattggc tcataggtaa gctcgctgtc acccagtacg      3060
gaggtgccag tagattatta gagacagtcg ccaatcgatg ttataccga gatgactgag       3120 tatcgaagct acattgtagc cgcacatagg accacccatc ttcatgttgg atccccgggc      3180
gagctcccaa aaaaaaaaaa aaaaaaaaaa aaaaaaacc g                           3221
```

<210> SEQ ID NO 8

<211> LENGTH: 3480
<212> TYPE: DNA
<213> ORGANISM: Artificial Sequence
<220> FEATURE:
<223> OTHER INFORMATION: Control nucleic acid

<400> SEQUENCE: 8

| | |
|---|---|
| aattcgtaat catgtcatag ctgtttcctg tgtgaaattg ttatccgctc acaattccac | 60 |
| acaacatacg agccggaagc ataaagtgta aagcctgggg tgcctaatga gtgagctaac | 120 |
| tcacattaat tgcgttgcgc tcactgcccg ctttccagtc gggaaacctg tcgtgccagc | 180 |
| tgcattaatg aatcggccaa cgcgcgggga gaggcggttt gcgtattggg cgctcttccg | 240 |
| cttcctcgct cactgactcg ctgcgctcgg tcgttcggct gcggcgagcg gtatcagctc | 300 |
| actcaaaggc ggtaatacgg ttatccacag aatcagggga taacgcagga agaacatgt | 360 |
| gagcaaaagg ccagcaaaag gccaggaacc gtaaaaaggc cgcgttgctg gcgttttcc | 420 |
| ataggctccg ccccctgac gagcatcaca aaaatcgacg ctcaagtcag aggtggcgaa | 480 |
| acccgacagg actataaaga taccaggcgt ttccccctgg aagctccctc gtgcgctctc | 540 |
| ctgttccgac cctgccgctt accggatacc tgtccgcctt ctcccttcg ggaagcgtgg | 600 |
| cgctttctca tagctcacgc tgtaggtatc tcagttcggt gtaggtcgtt cgctccaagc | 660 |
| tgggctgtgt gcacgaaccc cccgttcagc ccgaccgctg cgccttatcc ggtaactatc | 720 |
| gtcttgagtc aacccggta agacacgact tatcgccact ggcagcagcc actggtaaca | 780 |
| ggattagcag agcgaggtat gtaggcggtg ctacagagtt cttgaagtgg tggcctaact | 840 |
| acggctacac tagaagaaca gtatttggta tctgcgctct gctgaagcca gttaccttcg | 900 |
| gaaaaagagt tggtagctct tgatccggca acaaaccac cgctggtagc ggtggttttt | 960 |
| ttgtttgcaa gcagcagatt acgcgcagaa aaaaggatc tcaagaagat cctttgatct | 1020 |
| tttctacggg gtctgacgct cagtggaacg aaaactcacg ttaagggatt ttggtcatga | 1080 |
| gattatcaaa aaggatcttc acctagatcc ttttaaatta aaaatgaagt tttaaatcaa | 1140 |
| tctaaagtat atatgagtaa acttggtctg acagttacca atgcttaatc agtgaggcac | 1200 |
| ctatctcagc gatctgtcta tttcgttcat ccatagttgc ctgactcccc gtcgtgtaga | 1260 |
| taactacgat acgggagggc ttaccatctg gccccagtgc tgcaatgata ccgcgagacc | 1320 |
| cacgctcacc ggctccagat ttatcagcaa taaaccagcc agccggaagg gccgagcgca | 1380 |
| gaagtggtcc tgcaacttta tccgcctcca tccagtctat taattgttgc cgggaagcta | 1440 |
| gagtaagtag ttcgccagtt aatagtttgc gcaacgttgt tgccattgct acaggcatcg | 1500 |
| tggtgtcacg ctcgtcgttt ggtatggctt cattcagctc cggttcccaa cgatcaaggc | 1560 |
| gagttacatg atcccccatg ttgtgcaaaa aagcggttag ctccttcggt cctccgatcg | 1620 |
| ttgtcagaag taagttggcc gcagtgttat cactcatggt tatggcagca ctgcataatt | 1680 |
| ctcttactgt catgccatcc gtaagatgct tttctgtgac tggtgagtac tcaaccaagt | 1740 |
| cattctgaga atagtgtatg cggcgaccga gttgctcttg cccggcgtca atacgggata | 1800 |
| ataccgcgcc acatagcaga actttaaaag tgctcatcat tggaaaacgt tcttcggggc | 1860 |
| gaaaactctc aaggatctta ccgctgttga gatccagttc gatgtaaccc actcgtgcac | 1920 |
| ccaactgatc ttcagcatct tttactttca ccagcgtttc tgggtgagca aaaacaggaa | 1980 |
| ggcaaaatgc cgcaaaaaag ggaataaggg cgacacggaa atgttgaata ctcatactct | 2040 |
| tcctttttca atattattga agcatttatc agggttattg tctcatgagc ggatacatat | 2100 |
| ttgaatgtat ttagaaaaat aaacaaatag gggttccgcg cacatttccc cgaaaagtgc | 2160 |

```
cacctgacgt ctaagaaacc attattatca tgacattaac ctataaaaat aggcgtatca  2220 cgaggcccttt tcgtctcgcg cgtttcggtg atgacggtga aaacctctga cacatgcagc  2280
tcccggagac ggtcacagct tgtctgtaag cggatgccgg gagcagacaa gcccgtcagg  2340
gcgcgtcagc gggtgttggc gggtgtcggg gctggcttaa ctatgcggca tcagagcaga  2400
ttgtactgag agtgcaccat tcgacgctct cccttatgcg actcctgcat taggaagcag  2460
cccagtagta ggttgaggcc gttgagcacc gccgccgcaa ggaatggtgc atgcaaggag  2520
atggcgccca acagtccccc ggccacgggg cctgccacca tacccacgcc gaaacaagcg  2580
ctcatgagcc cgaagtggcg agcccgatct tccccatcgg tgatgtcggc gatataggcg  2640
ccagcaaccg cacctgtggc gccggtgatg ccggccacga tgcgtccggc gtagaggatc  2700
tggctagcga tgaccctgct gattggttcg ctgaccattt ccgggtgcgg gacggcgtta  2760
ccagaaactc agaaggttcg tccaaccaaa ccgactctga cggcagttta cgagagagat  2820
gatagggtct gcttcagtaa gccagatgct acacaattag gcttgtacat attgtcgtta  2880
gaacgcggct acaattaata cataacctta tgtatcatac acatacgatt taggtgacac  2940
tatagaatac aagcttgggc tgcaggtcga ctctagaaac tgggtagtaa ctgcggggc  3000 gaatgatgca ggcttcagaa attaaactca atagtatccg gtgtctcaat ctttttcggg  3060
ccaggcggcg gtggacgaca gacaatttta cgattttggt tccggtcaca accgcgccat  3120
acatgtcaag aatgaagtgg gcgaacgcta gaaaactgac gccagcaatt aagtgagtcg  3180
gggcgtggtg actcccacgt aaaaagcccc tacccgcac cgttacgaag tatcaaaacg  3240
ggacgcgcac gaaccgacga ttggtactgt ataagcggcc cgacgaactc aaaatcccaa  3300
gtgaatctat gaaatctaca tcgcgtttat aatctacggg gtgtaaacgg atgagaattg  3360
gccaaacgga ggcacacacg cgtgcaatgc gccgaccctg agaaaagtat catgtgcgtc  3420
ggccacagga tccccgggcg agctcccaaa aaaaaaaaaa aaaaaaaaaa aaaaaaaccg  3480
```